United States Patent [19]

Fiato et al.

[11] Patent Number: 4,689,313

[45] Date of Patent: Aug. 25, 1987

[54] IRON ON TITANIA FISCHER-TROPSCH CATALYST

[75] Inventors: Rocco A. Fiato, Scotch Plains; Edwin L. Kugler, Glen Gardner, both of N.J.

[73] Assignee: Exxon Research and Engineering Company, Florham Park, N.J.

[21] Appl. No.: 928,819

[22] Filed: Nov. 7, 1986

Related U.S. Application Data

[63] Continuation of Ser. No. 625,169, Jul. 2, 1984, abandoned, which is a continuation of Ser. No. 511,653, Jul. 7, 1983, abandoned.

[51] Int. Cl.$^4$ .............................................. B01J 27/22
[52] U.S. Cl. .................................... 502/177; 502/338; 518/717; 518/719; 518/720; 518/721
[58] Field of Search ............... 502/177, 338; 518/717, 518/719, 720, 721

[56] References Cited

U.S. PATENT DOCUMENTS 3,979,332  9/1976  Kiovsky et al. ..................... 502/3
4,154,751  5/1979  McVicker et al. .................. 518/717

FOREIGN PATENT DOCUMENTS 7150438  9/1982  Japan .
7703712  10/1977  Netherlands .
657528  9/1951  United Kingdom ................ 518/720
2078745  1/1982  United Kingdom .

OTHER PUBLICATIONS

Santos et al., "Metal-Support Interaction Between Iron and Titania for Catalysts Prepared by Thermal Decomposition of Iron Pentacarbonyl and by Impregnation" *Journal of Catalysis*, vol. 81, (May 1983), pp. 147-167.
Tatarchuk et al., "Physical Characterization of Fe/TiO$_2$ Model Supported Catalysts," *Journal of Catalysis*, vol. 70, (Apr. 1981), pp. 308-346.
Haensel, Kaiser Wilhelm Institut Fur Kohlnforschung, Mulheim, Office of Publication Board Dept. of Commerce, Wash. D.C. (1946), Report No. 284, pp. 4-6.

*Primary Examiner*—Andrew H. Metz
*Assistant Examiner*—Chung K. Pak
*Attorney, Agent, or Firm*—Joseph J. Dvorak

[57] ABSTRACT

A catalyst useful for producing substantially C$^2$+ alkane hydrocarbons from mixtures of CO and H$_2$ which comprises a mixture of iron carbide and ilmenite supported on titania wherein the ratio of the iron present in the supported iron carbide and ilmenite, calculated as Fe$_2$O$_3$, to the surface area of the titania support ranges from about $2 \times 10^{-3}$ to $25 \times 10^{-3}$ grams per square meter.

5 Claims, 1 Drawing Figure

EFFECT OF IRON ON TITANIA CONCENTRATION ON CO HYDROGENATION ACTIVITY

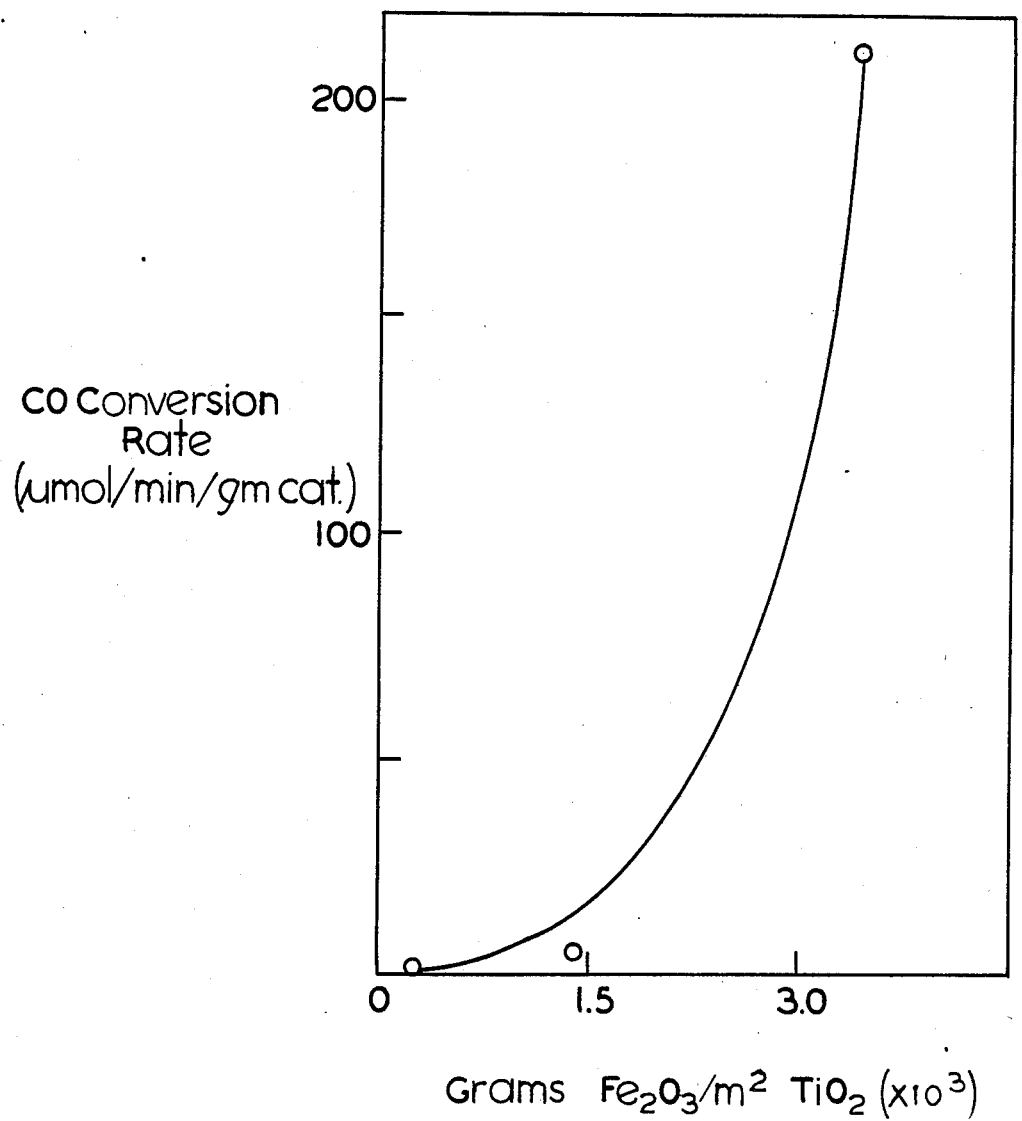

IRON ON TITANIA FISCHER-TROPSCH CATALYST

CROSS REFERENCE TO RELATED APPLICATIONS

This is a continuation of application Ser. No. 625,169, filed July 2, 1984, now abandoned, which is a continuation in part of application Ser. No. 511,653, filed July 7, 1983, abandoned.

BACKGROUND OF THE INVENTION

Field of the Invention

This invention relates to a Fischer-Tropsch catalyst comprising a mixture of iron carbide and ilmenite supported on titania. More particularly, this invention relates to a catalyst for producing substantially alkane hydrocarbons from mixtures of CO and $H_2$ comprising a mixture of iron carbide and ilmenite supported on titania wherein the ratio of the iron present in said supported iron carbide and ilmenite, calculated as $Fe_2O_3$, to the surface of the titania support ranges from about 2 to 25 milligrams per square meter.

The use of iron-titania mixtures as Fischer-Tropsch catalysts for converting mixtures of CO and $H_2$ to hydrocarbons is well-known to those skilled in the art. For example, U.S. Pat. No. 2,543,327 discloses titania promoted iron oxide for Fischer-Tropsch synthesis wherein the iron oxide is in the form of naturally occurring magnetite and preferably as Alan Wood ore. In this disclosure a typical catalyst is shown as prepared by mixing about 13,600 grams of Alan Wood ore with 98 grams of titania and 216 grams of potassium carbonate used as a promoter. The ratio of hydrogen to carbon monoxide disclosed as being preferably at least 2/1 and the results show that the catalyst has relatively poor activity with a large selectivity towards the production of methane and very little selectivity towards the production of $C_2+$ hydrocarbons. That is, the Fischer-Tropsch product was primarily methane. Similarly, British Pat. No. 1,512,743 also discloses a titania promoted, massive iron type of Fischer-Tropsch catalyst wherein iron oxide is mixed with titanium oxide, zinc oxide and potassium carbonate with the resulting mixture being sintered and then reduced for many hours at 500° C. Although this catalyst has relatively reasonable activity with regard to conversion of the CO and $H_2$ mixture, the product was primarily (i.e., about 73%) olefinic, unsaturated $C_2/C_4$ hydrocarbons and with only about 10% of $C_2/C_4$ saturated hydrocarbons or alkanes being produced. U.S. Pat. No. 4,192,777 and 4,154,751 while directed towards the use of potassium promoted Group VIII metal cluster catalysts in Fischer-Tropsch synthesis reactions, suggest that iron supported on titania would be useful Fischer-Tropsch catalysts but do not disclose the preparation of same. In their examples, they disclose iron on various supports other than titania with the amount of iron on the support generally being less than about 5 percent. U.S. Pat. No. 4,261,865 discloses an iron titanate-alkali metal hydroxide catalyst for preparing alpha-olefins from mixtures of CO and $H_2$. That is, the catalyst is not iron supported on titania along with an alkali metal hydroxide but rather an iron titanate compound.

Another example of a titania-promoted massive iron catalyst for Fischer-Tropsch synthesis may be found in the Volume 17, No. 3-4 React. Kinet. Catal. Lett., pages 373-378, (1981) titled "Hydrocondensation of $CO_2$ (CO) Over Supported Iron Catalysts". This article discloses an iron oxide, titania, alumina, copper oxide catalyst promoted with potassium. Similarly, in European patent application EP 0 071770 A2 Fischer-Tropsch catalysts are disclosed which include iron titania catalysts wherein the iron to titania ratio can be greater than 1/10. The actual iron-titania catalyst is not an iron supported on titania catalyst but an iron/titania catalyst produced by a coprecipitation technique wherein the active iron catalytic component is distributed throughout a titanium oxide matrix. Thus, the resulting catalyst was not iron supported on titania but rather a bulk phase iron/titania mixture which, when used for Fischer-Tropsch synthesis, produced predominantly olefins. The amount of olefins produced was generally greater than about 80% of the total hydrocarbon product.

With regard to iron/titania catalysts for Fischer-Tropsch wherein the iron is supported on titania, a 1982 article by Vannice, *Titania-Supported Metals as CO Hydrogenation Catalysts*, J. Catalysis, v. 74, p. 199-202 (1982), discloses the use of an iron/titania catalyst for Fischer-Tropsch synthesis wherein the amount of iron, calculated as metallic iron, is 5 percent of the iron/titania composite and the catalyst shows extremely little activity for Fischer-Tropsch synthesis.

An article by Reymond et al, *Influence of the Support or of an Additive on the Catalytic Activity in The Hydrocondensation of Carbon Monoxide by Iron Catalysts* in "Metal-Support and Metal-Additive Effects in Catalysis", B. Imelik et al. (Eds), Elsevier, Netherlands, p. 337-348 (1982), also discloses the use of iron/titania Fischer-Tropsch catalysts wherein the iron is supported on the titania. The iron/titania catalysts disclosed contain about 9.5 weight percent iron on titania and the activity of the resulting catalysts is presented as a function of the activation pretreatment of the iron/titania catalyst precursor. Thus, it was disclosed that if the precursor was pretreated in either helium or hydrogen at 250° C. there was relatively little activity for Fischer-Tropsch synthesis. Similarly, another composite treated in hydrogen for 15 hours at 500° C. showed no activity whatsoever. It is important to note that the catalytic activity was expressed only as a function of methane production using a 9/1 mole ratio of $H_2$/CO at one atmosphere pressure and a reaction temperature of 250° C.

SUMMARY OF THE INVENTION

It has now been discovered that substantially $C_2+$ alkane hydrocarbons can be produced from mixtures of CO and $H_2$ using a catalyst comprising iron supported on titania. Those skilled in the art know that ilmenite is an iron titanate having the formula $FeTiO_3$. The ratio of the iron present in said supported iron carbide and ilmenite, calculated as $Fe_2O_3$, to the surface area of the titania support will generally range from about 2 to 25 milligrams per square meter. By substantial alkane hydrocarbons is meant that more than about 50 wt.% of the hydrocarbon products, including methane, are alkane $C_2+$ hydrocarbons. In a preferred embodiment the catalyst will be pretreated with CO at elevated temperature prior to use.

BRIEF DESCRIPTION OF THE DRAWING

The FIGURE is a plot of CO conversion rate as a function of the iron loading level of a catalyst of this invention.

DETAILED DESCRIPTION

It is essential to this invention that a mixture of the iron carbide and ilmenite is supported on and not merely mixed with the titania support. The iron loading on the titania support must be sufficient to form a mixture of both iron carbide and ilmenite. In general, it has been found that this will occur if the iron loading, calculated as $Fe_2O_3$, is at least about 2 milligrams per square meter of titania support surface. It has been found that if the titania doesn't support at least about 2 milligrams of iron, calculated at $Fe_2O_3$ per $m^2$ of titania support surface, the catalyst will possess little or no activity for conversion of mixtures of CO and $H_2$ to hydrocarbons. On the other hand, it has been found that selectivity of the catalyst to alkane formation rapidly decreases if more than about 25 milligrams of iron, calculated as $Fe_2O_3$, per $m^2$ of $TiO_2$ support surface is loaded onto the titania support. Preferably, the amount of iron present in the iron carbide and ilmenite mixture on the titania support will range from about 2.8 to 8.3 milligrams, calculated at $Fe_2O_3$, per $m^2$ of titania support surface.

The catalyst will be prepared by depositing a suitable iron precursor component onto the titania support from a precursor solution using any of the well known techniques such as incipient wetness, multiple impregnation, pore-filling etc., the choice being left to the convenience of the practitioner. As has heretofore been stated, it is important for the iron precursor to be deposited onto the titania support as opposed to other methods for catalyst preparation such as co-precipitation or physical mixtures. After impregnation, the impregnate is dried to remove excess solvent and/or water therefrom. The dry impregnate can then be converted to a catalyst of this invention employing a number of different methods. In one method, the impregnate will be converted directly to a catalyst of this invention by contacting same with a CO containing reducing gas, preferably a reducing gas containing a mixture of CO and $H_2$. Thus, it will be appreciated to those skilled in the art that the catalyst of this invention can be formed from the impregnate in-situ in a Fischer-Tropsch hydrocarbon synthesis reactor. However, it is preferred to employ a sequential treatment of first contacting the dry impregnate with an $H_2$ containing reducing gas that does not contain CO to reduce the impregnate, followed by contacting the reduced impregnate with CO or a CO containing gas such as a mixture of CO and $H_2$ to form the catalyst of this invention. As a practical matter, it may be commercially advantageous to form the catalyst of this invention by subjecting the impregnate to calcining to convert the supported iron precursor component to iron oxide, followed by subsequent reduction and formation of the catalyst of this invention.

Promoter metals such as potassium or other alkali metals may be added via impregnation, etc. before the composite is contacted with a reducing atmosphere and/or CO containing gas to form the catalyst of this invention. In general, the amount of promoter metal present will range from about 0.5 to 5 wt.% based on the amount of iron (calculated as $Fe_2O_3$) supported on the titania.

If one desires to obtain a catalyst of this invention via a supported iron oxide route, then the dry impregnate will be calcined in air or other suitable oxidizing atmosphere at a temperature of from about 120° to 300° C. for a time sufficient to convert the supported iron precursor component to iron oxide. After the iron/titania impregnate has been calcined to convert the supported iron precursor compound to iron oxide, the iron oxide/titania composite, with or without one or more promoter metals, is preferably reduced in a hydrogen-containing, net-reducing atmosphere at a temperature broadly ranging from about 300°-500° C. for a time sufficient to convert the iron oxide to metallic iron. It has been found that if one tries to reduce the iron oxide/titania composite at a temperature below about 300° C. (i.e., 250° C.), the catalyst of this invention will not subsequently be formed.

Irrespective of the route one employs to form a catalyst of this invention, whether by reduction followed by contacting with CO, direct formation of the catalyst or through the supported iron oxide route, it is important not to contact the composite with a reducing gas at temperatures above about 500° C. Reduction temperatures exceeding about 500° C. will produce a catalyst which exhibits relatively low CO hydrogenation activity with less than 50% of the $C_2$+ hydrocarbons produced being alkanes. Further, even at a 500° C. reduction temperature a less effective catalyst will be produced if the reduction occurs for too long a time, i.e., about ten hours or more. Thus it will be appreciated that the temperature range for reducing the composite cannot be critically quantified with any degree of precision, inasmuch as there exists a time-temperature continuum for proper reduction.

In a preferred embodiment of this invention, the catalyst composite will first be reduced, followed by contacting with CO at temperatures ranging from about 200° to 500° C. and preferably 300° to 400° C. for a time sufficient to form a catalyst comprising a mixture of ilmenite and iron carbide supported on titania. It has been found that a CO treatment following hydrogen reduction dramatically improves the activity of the catalyst for CO conversion with only slight changes in product selectivity. A mixture of ilmenite and iron carbide on the titania support will also be achieved by treating the calcined iron/titania composite with a mixture of CO and $H_2$, but it is preferred to use the sequential treatment comprising hydrogen reduction followed by CO treatment. Further, when using this sequential treatment to produce a catalyst of this invention, it is preferred that the temperature used for the CO treatment be lower than that used for the hydrogen reduction. Thus, in general the CO treatment will occur at a temperature of about 100° to 200° C. lower than the temperature used for the hydrogen reduction.

It has also been discovered that, if a catalyst composite of this invention has been prepared by hydrogen reduction and then contacted in-situ, in a reactor, with a feedstream comprising a mixture of CO and $H_2$ to form a catalyst of this invention, the activity of the so-formed catalyst will be substantially increased by reducing or eliminating the hydrogen content of the feedstream, raising the temperature in the reactor an additional 50° to 150° C. for a short period of time (i.e., 3-5 hours), followed by reestablishing the original reaction conditions.

Predominantly $C_2$+ alkane hydrocarbons are produced from mixtures of CO and $H_2$ by contacting said mixtures with the catalyst of this invention at temperatures ranging from about 200° to 350° and preferably from about 250°-320° C. The reaction pressure will generally range from about 100-500 psig and more preferably from about 150-300 psig, although pressures outside this range may be used, if desired. However, if one goes too low in pressure (i.e., <50 psig), catalyst activity will be greatly reduced and methane production will predominate. Upper pressure limits will generally be dictated by economic considerations. The $H_2/CO$ mole ratio in the reaction zone will generally range from about 1/2 to 3/1, preferably from about 1/2 to 2/1 and still more preferably from about 1/2 to 1/1.

The invention will be more readily understood by reference to the following examples of which Examples 3 and 5 are directed to the claimed invention.

EXAMPLES

Example 1

In this experiment a number of iron supported on titania catalysts were prepared by impregnating, at room temperature, a titania powder (Degussa P-25) with aqueous solutions of ammonium trisoxalato ferrate containing different amounts of the iron salt. The resulting impregnates were dried in air. After drying, each impregnate was ground to a powder and calcined in air for at least one hour at 200° C. to form an iron oxide/titania composite. A 1-2 cc. sample of each composite was loaded into a ⅜ inch O.D. stainless steel tube reactor. The reactor was flushed with hydrogen at room temperature and atmospheric pressure. The reactor temperature was then brought up to 450° C. in flowing hydrogen (90 cm³/min) and maintained at these conditions for 1-2 hours. After this, the reactor was cooled to a temperature of 300° C. and the pressure increased to 150 psig. The hydrogen was then replaced with a 3/1 mole mixture of $H_2/CO$ at a flow rate (standard hourly velocity) of 3600 v/v/hr. The exit gas from the reactor was fed into a gas chromatograph for on-line analysis of $C_1$-$C_{15}$ hydrocarbons, CO, $CO_2$, and $N_2$.

The results of this experiment are plotted in the FIGURE in terms of CO conversion rate as a function of the iron loading level on the catalyst calculated as grams of $Fe_2O_3$ per m² of $TiO_2$ surface area. These results dramatically illustrate an unexpected, minimum critical iron loading level for Fischer-Tropsch activity of about $2\times10^{-3}$ grams of $Fe_2O_3$ per m² of titania.

Example 2

Another catalyst was prepared, consisting of $2\times10^{-3}$ grams of iron, calculated as $Fe_2O_3$, per square meter of titania support. This was prepared by mixing an aqueous solution of ferric nitrate with a titania slurry (Degussa P-25), with stirring, for an hour at 25° C. The mixture was then heated to 120° C. for a three hour period at a pressure of 45 mmHg pressure to remove the solvent and form a solid impregnate. The impregnate was then ground to a powder and dried overnight at 120° C. under vacuum, followed by drying in in air overnight at 130°-150° C. The dried, calcined, powdered composite was then pelletized at 5000-15,000 psi, crushed and sived to 20-80 mesh particles.

8.8 cm³ of the calcined catalyst composite was loaded into a ½ inch O.D. stainless steel tubular reactor which was then purged with hydrogen at 50° C. and atmospheric pressure. The pressure was then raised to 100 psig and a 9/1 mole mixture of $H_2/N_2$ introduced into the reactor at a rate of 100 cc/min. The temperature in the reactor was then increased to 500° C. at a rate of 6° C./min. and was maintained at these conditions for five hours to form the catalysts. The $H_2/N_2$ stream was then replaced with a Fischer-Tropsch feedstream consisting of a 1/1 mole ratio of $CO/H_2$ diluted with 10 volume percent nitrogen. The reactor pressure had been raised to 300 psig and the temperature reduced to 270° C. before the gas feed was introduced at a rate (standard hourly space velocity) of 500 v/v/hr. As in Example 1, the reactor effluent was fed into a gas chromatograph.

The results of this experiment are set forth in Table 1 and show that 57.2 percent of the hydrocarbon products were alkanes with less than 25 percent methane production.

Example 3

The experiment of Example 2 was repeated with the exception that the calcined catalyst composite was sequentially treated first with the 9/1 mole mixture of $H_2/N_2$ for five hours at 500° C. and then with a 9/1 mole ratio mixture of $CO/N_2$ for five hours at 350° C. The results of this experiment, also shown in Table 1, demonstrate the beneficial affects of the sequential hydrogen CO treatment in terms of increased CO conversion, higher alkane yield, and greater $C_5^+$ alkane yield.

Example 4

Another catalyst was prepared containing $4.2\times10^{-3}$ grams of iron, calculated as $Fe_2O_3$, per m² of titania support by adding a solution of 38.16 grams of ammonium trisoxalato ferrate in 60 milliliters of distilled water to 44.8 grams of titania (Degussa P-25). The resulting mixture was dried at 65° C. in air for three days. The resulting impregnated solid was ground to powder and heated at 200° C. for six hours to decompose the iron complex and calcine the impregnate. The resulting powder was subsequently cooled to room temperature and impregnated with 0.157 grams of potassium carbonate dissolved in 10 ml water. The mixture was dried in air at 120° C. for one hour to produce a potassium promoted composite wherein the amount of potassium was 4.28 percent based on the iron content, calculated as $Fe_2O_3$, of the calcined composite.

The potassium containing composite was then pelletized, crushed and sieved to 20-80 mesh particles, 8.8 cc of which were loading into a ½ inch stainless steel reactor and treated using the procedure given in Example 2. The results, shown in Table 2, illustrate less than about 5 percent olefin production.

Example 5

Another catalyst of this invention was prepared following the procedure of Example 2 to form a calcined composite which was pelletized, crushed and sieved wherein the catalyst contained $8.3\times10^{-3}$ grams of iron, calculated as $Fe_2O_3$, per square meter of titania support. This composite was reduced with a mixture of 20 percent hydrogen in helium for two hours at 450° C. and then cooled to 25° C. in the flowing gas. When room temperature was achieved, the hydrogen flow was stopped and oxygen was introduced into the flowing helium at a 2 percent level in order to passivate the reduced composite. X-ray diffraction patterns of this hydrogen reduced material showed $TiO_2$ (both anatase and rutile), $FeTiO_3$ (ilmenite) and $Fe^o$ (metallic iron). This same reduced sample was then treated with CO for one hour at 350° C. and cooled to room temperature in the same gas. After this, the sample was flushed with helium and then passivated with 3 percent oxygen in helium and the X-ray diffraction pattern measured again. It was found that the CO treatment as used in Example 3, had no effect on the X-ray powder diffraction pattern of the titania and ilmenite, but caused the X-ray diffraction pattern of metallic iron to disappear. Also, a broadened pattern of iron carbide $Fe_5C_2$ appeared after the CO treatment, indicating that CO converted the metallic iron to small particles of iron carbide.

TABLE 1

| Catalyst Treatment | $H_2$ | $H_2$, CO |
|---|---|---|
| Temperature, °C. | 270 | 270 |
| % CO Conversion | 26.8 | 59.5 |
| Wt. % Selectivity | | |
| $CH_4$ | 21.0 | 13.8 |
| $C_2^=$ | 0.8 | 1.0 |
| $C°_2$ | 16.2 | 13.5 |
| $C_3^=$ | 18.6 | 12.1 |
| $C°_3$ | 11.8 | 5.4 |
| $C_4^=$ | 2.4 | 4.1 |
| $C°_4$ | 6.2 | 5.3 |
| $C_5^+$ | 23.0 | 44.8 |
| $C_2^=-C_4^=/C°_2-C°_4$ | 0.64 | 0.71 |

Conditions: 2 MPa, 500 v/v/hr, 1:1 $H_2$:CO, $H_2$ pretreatment at 500° C., CO pretreatment at 350° C.
Composite $C_5^+$ determined by $N_2$ internal standard method.

TABLE 2

| Potassium Promoted Catalyst | |
|---|---|
| % CO Conversion | 89.2 |
| Wt. % Selectivity | |
| $CH_4$ | 18.9 |
| $C_2^=$ | 0.6 |
| $C°_2$ | 18.2 |
| $C_3^=$ | 2.2 |
| $C°_3$ | 17.8 |
| $C_4^=$ | 1.4 |
| $C°_4$ | 11.1 |
| $C_5^+$ | 29.8 |
| $C_2^=-C_4^=$ | 4.2 |
| $C°_2-C°_4$ | 47.1 |

Conditions: 290° C., 2 MPa, 500 v/v/hr, 1:1 $H_2$:CO, pretreatment with $H_2$ at 500° C. for 5 hr ($\neq$ 10 hr) and CO at 350° C. for 5 hr.
Composite $C_5^+$ determined by $N_2$ internal standard method.

What is claimed is:

1. A catalyst composition a consisting essentially of catalytic components supported on titania, said catalytic components being selected from the group consisting of a mixture of iron carbide and ilmenite and a mixture of iron carbide and ilmenite containing at least one alkali metal promoter wherein the ratio of supported iron present in said supported iron carbide and ilmenite, calculated as $Fe_2O_3$, to the surface area of said titania support ranges between about 2 to 25 milligrams per square centimeter, and wherein said catalyst has been formed by depositing an iron precursor salt of said catalytic component on said titania support, calcining said deposited salt and support to form a calcined composite and sequentially contacting said composite with a hydrogen containing reducing gas free of CO at elevated temperatures of from about 300° C. to about 500° C. for a time sufficient to reduce the calcined composite followed by contacting said reduced composite with CO at a temperature from about 100° to about 200° C. lower than the temperature used for said hydrogen contacting.

2. The catalyst of claim 1 wherein the amount of said at least one alkali metal promoter present ranges between about 0.5 to 5 wt.% based on the amount of iron, calculated as $F_2O_3$, present on the catalyst.

3. A process for forming a catalyst comprising a mixture of ilmenite and iron carbide supported on titania useful for producing substantially alkane hydrocarbons from mixtures of CO and $H_2$, said process comprising the steps of:
    (a) depositing iron on a titania support material from a solution of iron precursor compound in an amount such that the final catalyst will contain supported iron in an amount of at least about 2 milligrams of iron, calculated as $Fe_2O_3$, per square meter of titania support surface;
    (b) calcining the iron precursor supported on titania produced in step (a) at temperatures from about 120° C. to about 500° C. for a time sufficient to convert at least a portion of said supported iron to $Fe_2O_3$ whereby a calcine composite is formed; and
    (c) contacting said calcined composite formed in step (b) with a hydrogen containing reducing gas free of CO at a temperature of from between about 300° C. to about 500° C. for a time sufficient to reduce said calcined composite to form a reduced composite; and
    (d) contacting said reduced composite formed in step (c) with a CO containing gas at an elevated temperature of from about 100° C. to about 200° C. lower than the temperature used in step (c).

4. The process of claim 3 including the step of depositing at least one alkali metal on said titania support at least before step (c).

5. The process of claim 4 wherein the amount of said at least one alkali metal is in the range of about 0.5 to 5 weight percent based on the amount of iron, calculated as $Fe_2O_3$, supported on the titania.

* * * * *